(12) United States Patent
Gopalsamy et al.

(10) Patent No.: US 8,097,447 B2
(45) Date of Patent: Jan. 17, 2012

(54) SOLID NUTRIENT MEDIA USEFUL FOR ISOLATING AND IDENTIFYING ALKALIPHILIC BACTERIA

(75) Inventors: Gnanasekaran Gopalsamy, Gujarat (IN); Kalpana Haresh Mody, Gujarat (IN); Sumitra Datta, Gujarat (IN); Bhavanath Jha, Gujarat (IN)

(73) Assignee: Council of Scientific & Industrial Research, New Delhi (IN)

( * ) Notice: Subject to any disclaimer, the term of this patent is extended or adjusted under 35 U.S.C. 154(b) by 356 days.

(21) Appl. No.: 12/240,043

(22) Filed: Sep. 29, 2008

(65) Prior Publication Data

US 2009/0176268 A1 Jul. 9, 2009

(30) Foreign Application Priority Data

Jan. 7, 2008 (IN) .............................. 58/DEL/2008

(51) Int. Cl.
*C12N 1/20* (2006.01)
*C12Q 1/04* (2006.01)
*C12Q 1/00* (2006.01)

(52) U.S. Cl. ............................. 435/253.6; 435/34; 435/4

(58) Field of Classification Search ........................ None
See application file for complete search history.

(56) References Cited

U.S. PATENT DOCUMENTS 6,846,483 B2 * 1/2005 Kumar et al. ............... 424/93.46

OTHER PUBLICATIONS

Maeda et al. Alkalotolerant and Alkalophilic Bacteria in Seawater; Marine Ecology-Progress Series, vol. 2 (1980) pp. 105-108.*
Abbott et al. Evaluation of Kappa Carrageenan As a Substitute for Agar in Microbiological Media; Archytypes of Microbiology, vol. 128 (1981) pp. 355-359.*
Falahatpishe et al. Production and Purification of a Protease From an Alkalophilic *bacillus* Sp. 2-5 Strain Isolated From Soil; Iranian Journal of Biotechnology, vol. 5, No. 2 (Apr. 2007) pp. 110-113.*
Guffanti et al. Isolation and Characterization of New Facultatively Alkalophilic Strains of *bacillus* Species; Journal of Bacteriology, vol. 167, No. 3 (1986) pp. 766-773.*
F. Gutkind and Co. "Kappa-carrageenan (refined)" downloaded from http://www.fgutkind.com/downloads/KappaCarrageenan.pdf on Jun. 3, 2011.*
F. Gutkind and Co. "Agar Agar Food Grade" downloaded from Http://www.fgutkind.com/downloads/AgarAgarFoodGrade.pdf on Jun. 3, 2011.*
Datta et al. Novel Application of Kappa-Carrageenan: As a Gelling Agent in Microbiological Media to Study Biodiversity of Extreme Alkaliphiles; Carbohydrate Polymers, vol. 85 (2011) pp. 465-468.*

* cited by examiner

*Primary Examiner* — Rebecca Prouty
*Assistant Examiner* — Paul Martin
(74) *Attorney, Agent, or Firm* — Luedeka, Neely & Graham, P.C.

(57) ABSTRACT

The present invention relates to a solid nutrient media composition having alkaline pH, useful for isolating and identifying alkaliphilic microorganisms in pure form. The media composition consists of 5-15 g of carbon source, 2.5-10 g of peptone, 2.5-10 g of yeast extract, 0.5-1.5 g of dipotassium hydrogen phosphate; 0.1-0.5 g of magnesium sulphate heptahydrate, 30 μl-4 ml of super saturated solution of sodium hydroxide, 5-20 g of potassium chloride and 10-30 g of κ-carrageenan in one liter of distilled water. The potassium salt in combination with κ-carrageenan in specific proportion has been found to be a suitable replacement of agar in solidifying bacteriological media especially, for isolation of extreme alkaliphiles. The present invention also provides a method of using the solid nutrient media composition having alkaline pH to study biodiversity of cultivable alkaliphilic bacteria.

8 Claims, No Drawings

SOLID NUTRIENT MEDIA USEFUL FOR ISOLATING AND IDENTIFYING ALKALIPHILIC BACTERIA

FIELD OF THE INVENTION

The present invention relates to a solid nutrient media composition having alkaline pH, useful for isolating and identifying alkaliphilic microorganisms in pure form. More particularly, the present invention relates to A solid nutrient media composition having alkaline pH, wherein the media composition consisting of 5-15 g of carbon source, 2.5-10 g of peptone, 2.5-10 g of yeast extract, 0.5-1.5 g of dipotassium hydrogen phosphate; 0.1-0.5 g of magnesium sulphate heptahydrate, 30 µl-4 ml of super saturated solution of sodium hydroxide, 5-20 g of potassium chloride and 10-30 g of κ-carrageenan in one liter of distilled water.

BACKGROUND AND PRIOR ART OF THE INVENTION

Extremophiles are valuable resources in biotechnology. These organisms are adapted to grow at 100° C. in hot springs, at low temperature in cold polar seas, at high pressure in deep sea, at a very low and high pH values (pH 0-1 or pH 10-14) and at very high salt concentration up to 35%. Extremophiles and their cell components have been used in various industries as well as in environmental biotechnology. Industrial applications of alkaliphiles include exploitation of enzymes such as proteases, amylases, cellulases, and lipases which are commercialized and widely used mainly in detergent industries and bioremediation. Also, enzymes from extremophiles are expected to fill the gaps between biological and chemical processes due to their unusual properties.

Alkaline environment is a typical extreme environment which includes naturally occurring soda lakes, deserts, carbonated soil and industrial waste. The physiological properties of alkaliphilic microorganisms offer a multitude of potential applications in various fields of biotechnology and their utilization for commercial purposes. To employ the right bacterial culture for its exploitation, it is necessary to isolate them in pure form, which is only possible on solid media. To prepare solid media for alkaliphiles, it is necessary to add a gelling agent, which is stable in extreme alkaline condition. Apart from this, to study the biodiversity of cultivable alkaliphiles, it is necessary to purify them from mixed culture as individual colonies for which they are required to grow on a solid medium so that they grow as individual clones.

The use of solid culture media has been of fundamental importance to microbiological research since the nineteenth century. Desirable qualities of a solidifying agent for media include stability of gel over the temperature range of bacterial growth, resistance to digestion by bacteria, lack of syneresis, transparency, and the ability to form a reversible colloid. The solid culture medium must be firm enough to facilitate streaking and spreading. In addition, it is desirable that the gelling agent is relatively inexpensive and easily available. Since Koch first introduced agar as a gellifying agent in bacteriological media (Koch, R. Die Atiologie der Turberkulose. Berl. Klin. Wochenschr. (1882) 19: 221-230), it has become the primary gelling agent for solid media throughout the world. However, increased cost and shortage of resources have made a more readily available substitute for agar, desirable.

Carrageenan is a family of linear sulphated polysaccharides extracted from red seaweeds. Three basic types of carrageenan are available, which differ in the numbers and location of sulfated ester. These chemicals are large, highly flexible molecules, which curl around each other forming double helical structures in the presence of monovalent and divalent cations. This gives them the ability to form a variety of thermo-reversible gels at room temperature. Large scale cultivation of carrageenophytes is successfully carried out all over the world including India and hence there is no shortage of carrageenan yielding seaweeds. Good cultivation practices and simple extraction procedures leads carrageenan, a cheaper gelling agent as compared to agar. Carrageenan is widely used in the food and pharmaceutical industries as thickening, stabilizing and gelling agents.

A. W. Walker and A. A. Day in their paper entitled "Extracts from Irish moss as a substitute for bacteriological culture media" in Food Res. (1943) 8: 435-443 have described the extraction of carrageenan from Irish moss. They prepared the bacteriological media using agar and extracts of Irish moss as gelling agents and autoclaved and dispensed to plates. They observed the similar bacterial growth after 24 h incubation on the plates and also noted lack of syneresis with low concentration of carrageenan. However, they have introduced carrageenan as a substitute of agar for bacteriological culture media. The drawback is no mention made on pH of the media. They did not describe the media preparation having alkaline pH and isolation of alkaliphiles.

N. Watson and D. Apirion in their paper entitled "Substitute for agar in solid media for common usage in microbiology" in Appl. Env. Microbiol. (1976) 31: 509-513 have prepared media using various concentrations (1 to 4%) of commercially available gelling agents like agar, gelatin types I and II, $Ca^{++}$ and $K^+$ salts of carrageenan and autoclaved and allowed to solidify in small depression plates and incubated at 25 and 45° C. for gelling study. According to them, all the concentrations of gelatin types gave soft gel, where as all the concentrations of the $Ca^{2+}$ salt of carrageenan gave firm gel at 25° C., but soft gel at 45° C. while $K^{2+}$ salt of carrageenan gave firm gel at 25 and 45° C. They prepared enriched media containing either 1.5% agar or 2% carrageenan for growth comparison study of mutant E. coli stains. They observed that the patched colonies grew similarly on both the plates and reported the plates containing carrageenan were clearer and the colonies were more distinguishable. The drawbacks of the paper are the cultivation of mutant E. coli strains on carrageenan containing media and they have not mentioned about pH of the bacteriological media. They did not describe the preparation of solid carrageenan media in extreme alkaline pH and no mention is made on the cultivation of alkaliphilic bacteria.

A. D. Lines in his paper entitled "Value of the K+ salt of carrageenan as an agar substitute in routine bacteriological media" in Appl. Env. Microbiol. (1977) 34: 637-639 has described the preparation of media having pH 7.6 with two different gelling agents, i.e. agar (1.2 to 2%) and carrageenan (2%). He assessed the suitability of carrageenan containing media by studying the parameters like (i) appearance, (ii) gel strength, (iii) ease of preparation, (iv) growth support including retention of antigenic characteristics, (v) resistance to digestion, and (vi) utilization of components by microorganisms. He reported 2% suspension of carrageenan retained its gel strength at 45° C. than their respective agar. However, 2% carrageenan looses its gel strength at 60° C. where higher concentration (2.4% carrageenan) overcomes the problem. He also mentioned that melting and gelling temperatures of carrageenan is similar to those of agar. He concluded that carrageenan containing media supports the growth of microbes with colony morphology, time of growth, viability, and pigment productions which were identical to those of agar preparations. The drawbacks are the preparation of bacteriological media using agar and carrageenan having pH 7.6 and comparison of only colony characteristics on both the media. However, he did not describe the preparation of alkaline solid media having pH greater than 7.6 and no mention is made on the cultivation of alkaliphilic bacteria.

Epifanio et al in their paper entitled "Carrageenan from *Eucheuma striatum* (Schmitz) in bacteriological media" in Appl. Env. Microbiol. (1981) 41: 155-158 have described the bacteriological media composed of either agar or carrageenan as gelling agent, 15 g; with peptone, 5 g; sodium chloride, 8 g; beef extract, 3 g; distilled water 1000 ml. The above media were autoclaved and used to prepare solid plates, slants and butts. Bacterial cultures were inoculated and incubated under conditions required by the organisms. They studied that the carrageenan and agar gels were sufficiently firm to permit effective and convenient streaking on plates and slants, requiring a break force of 520 to 868 $g/cm^2$ and 536 to 800 $g/cm^2$ respectively. They compared physiological and microscopical characters of microbes grown on both, agar and carrageenan containing media. The drawbacks are they have not mentioned pH of the bacteriological media and they compared physiological and microscopic characters of microbes. However, they did not carry out preparation of alkaline solid media and isolation of alkaliphiles.

M. Reeslev and A. Kjoller in their paper entitled "Comparison of biomass dry weights and radial growth rates of fungal colonies on media solidified with different gelling compounds" in Appl. Env. Microbiol. (1995) 61: 4236-4239 have described the media with different gelling agents for cultivation of three different fungi. They prepared solid media having pH 6.0 with agar, pluronic F-127, carrageenan X-4910 or carrageenan X-4910 overlaid with cellophane. They reported the similar fungal growth and visual appearance of the colonies on both gelled media, e.g., the pigmentation on carrageenan X-4910 was generally the same as that on agar. The drawbacks are preparation of media having acidic pH (6.0) using carrageenan as an alternative gelling agent to that of agar and they cultivated fungi for physiological studies. They did not prepare solid media having alkaline pH and also no mention is made on cultivation of bacteria.

Laserna et al in their paper entitled "Carrageenan from *Eucheuma striatum* (Schmitz) in media for fungal and yeast cultures" in Appl. Env. Microbiol. (1981), 42:174-175 have prepared plates and slants of potato dextrose for fungi and cornmeal for yeast with agar (at pH 7.1 to 7.28) and carrageenan (at pH 7.18 to 7.46) in the same concentration (1.5%) and a loopful of each inoculum was streaked on the plates and slants and incubated at 27° C. for 2 to 7 days for fungi and 30° C. for 2 days for yeast. They observed the similar growth of fungi and yeasts on agar and carrageenan containing media. The drawbacks are preparation of media having neutral pH and cultivation of fungi and yeast. They did not carry out the preparation of alkaline solid media having pH greater than 7.5 and no mention made on the cultivation of bacteria.

Rambach Alain in US patent Application No. 20030129731 dated on 10 Jul. 2003 and 20060134730 dated on 22 Jun. 2006 have disclosed a new dehydrated culture medium, soluble in cold water containing κ- or τ-carrageenan as a gelling agent. He described the method of sample analysis by mixing it with dehydrated medium, dissolving in water, and allowing to form gel followed by incubation at 37° C. for 24 to 48 h. He used the medium to identify contaminants from samples of food industries and health care hospital. The drawback of the process is that κ- or τ-carrageenans are not soluble in cold water and hence it is essential to either boil or autoclave the culture medium. Moreover, he carried out the work of detection and identification of contaminant bacteria from food industry and care hospital. Also, he did not describe alkaline solid media preparation and isolation of alkaliphiles in extreme condition.

Read Taintor in his patent (U.S. Pat. No. 7,018,828 dated 28 Mar. 2006) entitled "Microbial culture medium containing agar and τ-carrageenan", has disclosed the culture media containing both, agar and carrageenan, for identification and antimicrobial susceptibility testing of unknown microorganisms. He used agar as a gelling agent and carrageenan as a stabilizing agent to improve the shelf life of agar containing media. The carrageenan-infused culture media resulted in a reduction of syneresis, thus providing potential improved performance of the media. The drawbacks are i) he used both, agar and carrageenan as a gelling agents, the purpose of addition of τ-carrageenan to increase the shelf life ii). He did not mention about pH of microbiological culture media. Also, he did not prepare microbiological media having high alkaline pH and no mention made on the isolation, purification and identification of alkaliphilic bacteria.

Shungu et al in their paper entitled "Gelrite as an agar substitute in bacteriological media" in Appl. Env. Microbiol. (1983) 46: 355-359 has described the preparation of blood agar (tryptic soy broth with 5% sheep blood) and selective media such as bismuth sulphite, brilliant green, eosin methylene blue and MacConkey using agar and gelrite as the gelling agents. They compared the growth of 50 different species on a variety of common as well as differential, selective and enrichment media gelled by agar and gelrite. After inoculation, the plates were incubated at 35° C. for 24 to 72 h. They reported all the test parameters like colony characteristics, biochemical reactions, haemolytic patterns, and plating efficiency were comparable on the media gelled by agar or gelrite. The drawbacks are: (1) they used gelrite as an alternative gelling agent; (2) no mention is made on pH of the media and (3) application of these media for isolation, identification and enumeration of bacteria. (4) They did not describe the use of carrageenan as a gelling agent; no mention is made on the preparation of media having alkaline pH and use of media for the isolation of alkaliphiles.

B. J. Bromke and M. Furiga in their paper entitled "Carrageenan is a desirable substitute for agar in media for growing *Trichomonas vaginalis*" in J Microbiol. Methods (1991) 13: 61-65 have used many commercially available gelling agents as potential substitutes for agar in media for growing a protozoan, *Trichomonas vaginalis*. According to them, only carrageenan (0.3 g/100 ml) fulfilled all the requirements for growth, normal morphology and proper harvesting of trichomonads with cost-efficiency. However, the drawback is that the paper deals only with the cultivation of protozoa. Also, no mention is made on suitability of κ-carrageenan as gelling agent, specifically for the isolation, purification and identification of alkaliphilic bacteria.

I. A. Abbott and F. A. Chapman in their paper entitled "Evolution of κ-carrageenan as a substitute for agar in microbiological media" in Arch. Microbiol. (1981) 128: 355-359 have mentioned that carrageenan was superior in comparison to agar with respect to transparency of the medium. They have used 71 samples of the colloid κ-carrageenan extracted from 12 seaweed species and reported that all the samples had a lower melting temperature (less than 67° C.) than agar and a gelling (setting) temperature between 16° C. and 51° C. They also added all the gelling samples did not show syneresis in the slant as well as in the plates. They observed all the test microorganisms grew well on both κ-carrageenan based media and agar containing media. The drawbacks of the paper are application of these media for cultivation of microorganisms and no mention is made about pH of the microbiological media. They did not describe the preparation of carrageenan based solid media and isolation of alkaliphilic bacteria.

P. L. Rule and A. D. Alexander in their paper entitled "Gellan gum as a substitute for agar in leptospiral media" in J. Clin. Microbiol. (1986) 23: 500-504 have described the preparation of media with gellan gum and agar as gelling agents for the cultivation of both pathogenic and saprophytic *Leptospira*. They observed the similar colonial growth on agar and on gellan gum media and reported that the gellan gum containing media has a long-term stability up to 9-12 months and hence preferred as a maintenance medium. The drawbacks are use of gellan gum as a gelling agent and cultivation of *Leptospira*. Also, they did not describe the use of carrageenan as a gelling agent, preparation of extreme alkaline media and isolation and cultivation of alkaliphiles.

Jain et al in their paper entitled "Guar gum: a cheap substitute for agar in microbial culture media" in Letts. Appl. Microbiol. (2005) 41: 345-349 have described the preparation of agar and guar gum gelled media for bacterial and fungal studies. They have cultivated 11 bacteria and 12 fungi on media solidified with either guar gum or agar. They observed the normal bacterial and fungal growth on the media gelled with guar gum and reported similar bacterial and fungal structures during the microscopical examination. They examined the bacterial enumeration studies by serial dilution and pour plate method and found that similar bacterial counts on both agar and guar gum. The drawbacks are use of guar gum as gelling agent, cultivation of bacteria and fungi and no mention is made about pH of the media. They did not describe the application of κ-carrageenan as gelling agent, preparation of alkaline solid media and isolation of alkaliphiles.

In view of the above citations, the inventors of the present invention understood the need of a solid nutrient media composition having alkaline pH, useful for isolating and identifying alkaliphilic microorganisms in pure form, which obviates the drawbacks of the mentioned citations.

OBJECT OF THE INVENTION

The main object of the invention is to provide a solid nutrient media composition having alkaline pH, useful for isolating and identifying alkaliphilic microorganisms in pure form.

Yet another object of the present invention is to provide a process for the preparation of a solid nutrient media composition having alkaline pH in the range of 8.0-13.5.

Still another object of the present invention is to provide a method of isolating and identifying alkaliphilic microorganisms in pure form using the said solid nutrient media composition having alkaline pH in the range of 8.0-13.5.

Yet another object of the present invention is to purify different extreme alkaliphilic bacteria based on the colony morphology and biochemical characteristics and various molecular identification tools.

Still another object of the present invention is to study biodiversity of cultivable alkaliphilic bacteria.

SUMMARY OF THE INVENTION

The present invention provides a solid nutrient media composition having alkaline pH, useful for isolating and identifying alkaliphilic microorganisms in pure form, wherein the media composition consisting of 5-15 g of carbon source, 2.5-10 g of peptone, 2.5-10 g of yeast extract, 0.5-1.5 g of dipotassium hydrogen phosphate; 0.1-0.5 g of magnesium sulphate heptahydrate, 30 μl-4 ml of super saturated solution of sodium hydroxide, 5-20 g of potassium chloride and 10-30 g of κ-carrageenan in one liter of distilled water.

The present invention further provides a method for isolation, purification and identification of extreme alkaliphilic bacteria by formulating a new medium using carrageenan as gelling agent with a view to understand biodiversity of cultivable alkaliphiles, as agar looses its gelling properties under extreme alkaline condition.

Thus, the present invention describes formulation of a new extreme alkaline solid medium by identifying an alkali stable and cheaper gelling agent as an alternative of agar for the isolation of extreme alkaliphiles in pure form.

Accordingly, the present invention provides a solid nutrient media composition having alkaline pH, useful for isolating and identifying alkaliphilic microorganisms in pure form, wherein the media composition per liter of distilled water consisting of 5-15 g of carbon source, 2.5-10 g of peptone, 2.5-10 g of yeast extract, 0.5-1.5 g of dipotassium hydrogen phosphate; 0.1-0.5 g of magnesium sulphate heptahydrate, 30 μl-4 ml of super saturated solution of sodium hydroxide, 5-20 g of potassium chloride and 10-30 g of κ-carrageenan.

In an embodiment of the present invention, the said media is having pH in the range of 8.0 to 13.5.

Yet in an embodiment of the present invention, the carbon source used is selected from the group comprising sucrose, glucose, starch.

Still in an embodiment of the present invention, the said media is being stabilized at pH 13.5 by using k-carrageenan as gelling agent.

Yet in another embodiment of the present invention, the super saturated solution of sodium hydroxide alkali is being used for maintaining the pH of the medium in the range of 8.0 to 13.5.

Still in another embodiment of the present invention, a specific proportion of κ-carrageenan and potassium chloride is maintained in the range of ratio of 1:2-2:3 to obtain the desired gel strength of 230-810 g/cm2 of the said solid media at pH of 12.5-13.5.

Further in an embodiment of the present invention, a process for preparing a solid nutrient media composition having alkaline pH, comprising the following steps of:
  a) preparing a culture medium by mixing the ingredients in the following proportions: 5 g-15 g of carbon source, 2.5-10 g of peptone, 2.5-10 g of yeast extract, 0.5-1.5 g of dipotassium hydrogen phosphate; 0.1-0.5 g of magnesium sulphate heptahydrate, 5-20 g of potassium chloride and 10-30 g of κ-carrageenan in one liter of distilled water;
  b) sterilizing the media as obtained from step (a) at standardized condition (121° C. for at least 15 minutes) or varying condition to obtain the desired solid nutrient media; and
  c) adjusting the pH of the medium as obtained from step (b) in the range of 8 to 13.5 using 30 μl to 4 ml of saturated solution of sodium hydroxide.

Yet in another embodiment of the present invention, a method of isolating and identifying alkaliphilic microorganisms in pure form, using the said solid nutrient media composition, wherein the said method comprising the following steps of:
  i. inoculating the suspension of alkaline soil sample and alkaline effluent by spreading technique on the said solid nutrient media having pH in the range of 8.0 to 13.5 according to claim 1 to obtain isolated colonies of alkaliphiles;
  ii. incubating the microbial plates as obtained from step (i) at 37±2° C. for a period of 24-72 hours;

iii. purifying individual colony from the plates as obtained from step (ii) and re-inoculating the sample on the same fresh solid medium and growing at 37±2° C. for a period of 24-72 hours;
iv. transferring individual pure bacterial colony as obtained from step (iii) on the slants containing same solid nutrient medium;
v. identifying the bacterial culture as obtained from step (iv) using standardized cultural, morphological and biochemical tests and molecular methods;
vi. studying alkaline tolerance, salt tolerance and other properties of cultivable alkaliphilic bacteria of bacteria as obtained from step (v).

Still in another embodiment of the present invention, the individual colonies are purified based on their size, shape and the pigments.

Yet in another embodiment of the present invention, the size of individual colonies being in the range of 0.5-3.0 mm, shape being selected from the group comprising flat, concave or convex and pigments being selected from the group comprising translucent, white, cream or yellow.

Further in another embodiment of the present invention, the isolated colonies were subjected to identify alkaliphilic bacteria using biochemical tests and molecular tools.

Still in another embodiment of the present invention, the identification profile was used to determine biodiversity of the cultivable alkaliphilic bacteria.

BRIEF DESCRIPTION OF THE TABLES

In the following tables accompanying the specification:

Table 1 shows the requirement of super saturated NaOH solution (110 g NaOH/100 ml DW) in 100 ml medium with respect to pH;

Table 2 shows the effect of κ-carrageenan and potassium chloride (KCl) concentration on gel quality and gel strength of the medium at pH 13.0;

Table 3 shows the effect of κ-carrageenan and KCl concentration on gel quality and gel strength of the medium having pH 13.5;

Table 4 shows the growth of various isolates of alkaliphiles on the solid media having different pH; and Table 5 shows the salt tolerance of various alkaliphilic bacteria.

DETAILED DESCRIPTION OF THE INVENTION

The present invention provides a solid nutrient media composition having alkaline pH, useful for isolating and identifying alkaliphilic microorganisms in pure form. The solid nutrient media composition consists of following ingredients: 5-15 g of carbon source, 2.5-10 g of peptone, 2.5-10 g of yeast extract, 0.5-1.5 g of dipotassium hydrogen phosphate; 0.1-0.5 g of magnesium sulphate heptahydrate, 30 µl-4 ml of super saturated solution of sodium hydroxide, 5-20 g of potassium chloride and 10-30 g of κ-carrageenan in one liter of distilled water.

The present invention describes the use of □-carrageenan as a gelling agent in the said solid nutrient media composition that is used to maintain, grow and isolate extreme alkaliphilic microorganisms.

The culture media contains all the elements that most bacteria need for growth and are non-selective, so they are used for the general cultivation and maintenance of alkaliphilic bacteria.

The term "alkaliphilic bacteria" are those archaebacteria which can either tolerate or require extreme alkaline pH and hence described as alkali-tolerant or alkaliphilic. They are classified as extremophiles that thrive in alkaline environments such as soda lakes, deserts, carbonate-rich soils and industrial waste.

The culture media disclosed can be employed to culture only alkali-tolerant and extreme alkaliphiles. In preferred embodiments, a culture medium of the invention contains either monosaccharide or disaccharide or polysaccharide (e.g., glucose or sucrose or starch) to provide carbon source for growth of bacteria and various $K^+$ and $Mg^{++}$ salts (e.g., dipotassium hydrogen phosphate and magnesium sulphate) needed for the growth of bacteria. The culture medium also contains protein hydrolysates (e.g., peptone and yeast extract) to provide nitrogen source to bacteria. The culture medium contains sodium hydroxide to provide alkaline environment for the growth of alkaliphilic bacteria. The culture medium also contains a gelling agent (e.g., κ-carrageenan or agar) to obtain solid media required for the isolation of alkaliphiles in pure form.

Sodium hydroxide was used to increase the pH of the inventive media. The known quantity of sterilized super saturated sodium hydroxide solution is added after autoclaving of the medium to prepare the culture medium with different pH viz. 8.0, 9.0, 10.0, 11.0, 11.5, 12.0, 12.5, 13.0 and 13.5. To achieve pH higher than 13.5, high volume of sodium hydroxide solution was required.

The inventive media contain carbon source either glucose or sucrose or starch. The alkaliphiles could grow in all the sugar containing media. Sucrose or starch containing media is more stable in high alkaline condition as compared to glucose. Moreover, sucrose containing media yielded better growth and larger colonies of alkaliphiles. Therefore, sucrose containing media is used to prepare the media having different pH from 8.0 to 13.5 as mentioned above.

As the agar could not form gel in extreme alkaline pH greater than 12.5 due to its de-polymerization, which led to loss of its gelling properties, in the inventive media, κ-carrageenan is used as an alternative gelling agent to provide sufficient gel strength to the media having pH from 8.0 to 13.5 as mentioned above, in the presence of potassium chloride. For gel formation κ-carrageenan requires potassium or calcium ions.

The requirement of κ-carrageenan and potassium chloride concentration, to provide required gel strength, was established at pH 13.0 and 13.5 by measuring the gel strength of inventive media. Gel strength was measured by a gel tester (kiya seisakusho ltd, Tokyo). It was observed that at pH 13.0, 1.5% κ-carrageenan along with 1% KCl yielded required gel strength where as at pH 13.5, 2% of κ-carrageenan and 1.5% of KCl are required.

The alkaliphiles could grow more efficiently with the inventive media as compared to conventional culture media. In this way, the present invention permitted greater application in detecting alkaliphiles; facilitate detection in smaller samples or samples with lower microbial loads as compared to conventional techniques.

On the said medium (pH 12) alkaline soil suspension and alkaline effluents were inoculated by spreading with a view to isolate alkaliphilic bacteria in the form of pure individual colonies. The culture plates were incubated at 37° C. for 48 h. and the isolates were purified by repeated streaking.

To isolate individual colonies in the pure form, a single colony of alkaliphilic bacteria was transferred to another plate containing sterilized medium using sterilized inoculation loop. This introduces a particular bacterial colony to a substrate which provides them nutrients. The plate is incubated at 37° C. for 24 to 48 h, to allow the bacteria to reproduce. At the end of incubation, there will be enough bacterial colonies of a single culture in the form of isolated colonies which will be used to study colony morphology and biochemical characteristics of the culture.

The inventive culture media disclosed were used to isolate extreme alkaliphilic bacteria by inoculating the pure alkaliphilic bacterial cultures grown on the alkaline solid media having pH higher than 12.0.

The isolated cultures were streaked on media having different pH between 8.0 and 13.5 and incubated at 37° C. for 48 h. Alkali tolerance and aklaliphilicity of each culture was established.

Salt tolerance of each culture was established by inoculating individual culture on the inventive culture media having pH 12, containing salt concentration from 1 to 15%. The plates were incubated at 37° C. for 48 h. Halo-alkaliphilic nature of isolated bacterial cultures was identified based on this study.

The pure, isolated bacterial cultures were subjected to preliminary identification based on colony characteristics, morphological and bio-chemical features. Molecular identification of promising alkaliphilic/halo-alkaliphilic bacterial cultures, using 16 srRNA technique was carried out and thus, the inventive culture media disclosed can be used to study the biodiversity of cultivable extreme alkaliphiles.

According to the present invention, it is provided with a solid nutrient medium having pH from 8.0 to 13.5, for the isolation of alkaliphilic bacteria. The present invention also relates to a novel medium composition in which κ-carrageenan is used as a gelling agent which is stable in extreme alkaline pH. Thus, the present invention relates to a method for isolation, purification and identification of extreme alkaliphilic bacteria on a solid medium containing κ-carrageenan as a gelling agent.

It was observed that agar is not a suitable gelling agent to prepare solid medium having pH higher than 12.5 due to its de-polymerization. Application of κ-carrageenan as an alternate gelling agent at extreme alkaline pH is being reported for the first time. κ-carrageenan is easily available and stable under extreme alkaline condition up to pH 13.5. Here, κ-carrageenan and agar can be used as a gelling agent up to pH 12.5. However, at pH greater than 12.5, κ-carrageenan was found to be the only suitable gelling agent.

The said media with a pH range from 8.0 to 13.5 and salt concentration from 1.0 to 15% are used to isolate extreme alkaliphiles and halo-alkaliphiles in pure form which can be exploited individually or in the form of a consortium for industrial applications.

The objective of formulating a new stable solid extreme alkaline medium was to identify isolated individual colonies using conventional and molecular tools and techniques which would ultimately used to study biodiversity of cultivable alkaliphiles.

The inventive steps adopted in the present invention include i) the culture media prepared for the isolation, purification and identification of extreme alkaliphiles; ii) the wide pH ranges from 8.0 to 13.5 is used to prepare the alkaline solid media; iii) the culture media having gelling agent κ-carrageenan, which is stable at pH greater than 12.5; iv) the inventive culture media containing sodium hydroxide is to obtain pH from 8.0 to 13.5; v) the common gelling agent agar is replaced due to instability in extreme alkaline pH; vi) the alternative gelling agent, κ-carrageenan is preferred as it is more alkali stable, economical and easily available due to high availability of raw material; vii) the κ-carrageenan gave required gel strength at 1.5-3.0% concentration in presence of 1-1.5% of KCl at pH 12 to 13.5; viii) the inventive culture media is used to isolate extreme alkaliphiles in the form of individual colonies; ix) the culture media is used to study biodiversity of cultivable extreme alkaliphiles.

The following examples are given by way of illustration of the present invention and therefore should not be construed to limit the scope of the present invention.

Example 1

Alkaline solid medium was used as a basal medium having composition (g/l) sucrose 10 g; peptone 5 g; yeast extract 5 g; $K_2HPO_4$ 1.0 g; $MgSO_4.7H_2O$ 0.2 g; potassium chloride 10 g and a solidifying agent κ-carrageenan 15 g. The solidification agent κ-carrageenan forms the gel in presence of potassium chloride. The pH 10.0 of the medium was adjusted by adding 160 μl of sterilized super saturated solution of sodium hydroxide (110 g NaOH/100 ml distilled water). Media with different pH were prepared by adding known quantity of sodium hydroxide after autoclaving is shown in Table 1.

TABLE 1

Requirement of super saturated NaOH solution (110 g NaOH/100 ml DW) in 100 ml medium with respect to pH

| NaOH solution (μl) | pH achieved |
|---|---|
| Nil | 7.0 ± 0.2 |
| 30 | 8.0 ± 0.1 |
| 80 | 9.0 ± 0.1 |
| 130 | 9.60 ± 0.1 |
| 160 | 10.0 ± 0.1 |
| 200 | 10.4 ± 0.1 |
| 250 | 11.0 ± 0.1 |
| 300 | 11.5 ± 0.1 |
| 400 | 12.0 ± 0.1 |
| 500 | 12.5 ± 0.1 |
| 1500 | 13.0 ± 0.1 |
| 3000 | 13.3 ± 0.1 |
| 4000 | 13.5 ± 0.1 |

Example 2

The alkaline solid media used as a basal medium having composition (g/l) sucrose 10 g; peptone 5 g; yeast extract 5 g; $K_2HPO_4$ 1.0 g; $MgSO_4.7H_2O$ 0.2 g; potassium chloride 10 g and a solidifying agent κ-carrageenan 15 g. The pH of the medium was adjusted to 12.0 by adding 400 μl of sterilized super saturated solution of sodium hydroxide. The gel of the medium was strong enough for inoculation of the culture suspension by spreading technique.

Example 3

The alkaline solid media used as a basal medium having composition (g/l) sucrose 10 g; peptone 5 g; yeast extract 5 g; $K_2HPO_4$ 1.0 g; $MgSO_4.7H_2O$ 0.2 g; potassium chloride 15 g and a solidifying agent κ-carrageenan 20 g. The pH of the medium was adjusted to 13.0 by adding 1.5 ml of sterilized super saturated solution of sodium hydroxide. The gel of the medium was strong enough for inoculation of the culture suspension by spreading technique.

Example 4

The alkaline solid media used as a basal medium having composition (g/l) sucrose 10 g; peptone 5 g; yeast extract 5 g; $K_2HPO_4$ 1.0 g; $MgSO_4.7H_2O$ 0.2 g; potassium chloride 15 g and a solidifying agent κ-carrageenan 25 g. The pH of the medium was adjusted to 13.5 by adding 4 ml of sterilized super saturated solution of sodium hydroxide. The gel of the medium was strong enough for inoculation of the culture suspension by spreading technique.

Example 5

The alkaline solid media used as a basal medium having composition (g/l) sucrose 10 g; peptone 5 g; yeast extract 5 g; $K_2HPO_4$ 1.0 g; $MgSO_4.7H_2O$ 0.2 g; and a solidifying agent agar 20 g. The pH of the medium 10.0 and 12.0 was adjusted by adding 160 and 400 μp of sterilized super saturated solution of sodium hydroxide respectively. 2% agar provided required gel strength to solid media which enabled inoculation by spreading method.

Example 6

The alkaline solid media used as a basal medium having composition (g/l) sucrose 10 g; peptone 5 g; yeast extract 5 g; $K_2HPO_4$ 1.0 g; $MgSO_4.7H_2O$ 0.2 g; and a solidifying agent agar 20 g for pH 12.0 and 25 g for pH 12.5 and higher. The pH of the medium was adjusted to 12, 12.5, 13.0 and 13.5 by adding 400 μl, 500 μl, 1.5 ml and 4 ml respectively of sterilized super saturated solution of sodium hydroxide. In the media with pH up to 12, 2% agar yielded necessary gel strength, for medium having pH 12.5, 2.5% agar provided required gel strength on which spreading of sample is possible. However, on the media having pH greater than 12.5, 2.5% and even 3% agar could not offer adequate gel strength. Here, agar could not form gel in extreme alkaline pH greater than 12.5 due to its depolymerization, which led to loss of its gelling properties.

Example 7

Horikoshi medium was modified with a view to isolate extreme alkaliphilic bacteria, as the former had pH only up to 10.6. In the modified medium glucose is replaced by sucrose, agar is replaced by κ-carrageenan and KCl and pH was adjusted to 10.0, 12.0, 13.0 and 13.5 by adding the known volume of sterilized super saturation solution of sodium hydroxide as mentioned in Table 1. Sucrose containing medium yielded isolated bigger colonies as compared to glucose containing medium.

Example 8

Normally used κ-carrageenan and KCl concentration (1% both) give high-quality gel with high strength. Same concentrations were used for alkaline media having pH 10.0, 12.0, 13.0 and 13.5 and the gel strength was 400, 380, 350 and less than 100 g/cm², respectively. This indicated that the medium prepared using κ-carrageenan as gelling agent at 1% concentration does not provide requisite gel strength, to the medium having alkaline pH, to facilitate streaking for separation of bacteria in the form of isolated colonies due to low gel strength of the medium.

Example 9

Optimum concentration of κ-carrageenan and KCl in the medium to obtain desired gel strength for the isolation of extreme alkaliphilic bacteria was determined by varying κ-carrageenan and KCl concentration in the medium having 1.5 ml of super saturated sodium hydroxide solution (pH 13.0). Table 2 describes quality of gel obtained and gel strength of the medium with respect to κ-carrageenan and KCl concentration. The culture medium having pH 13.0, containing 1.5% κ-carrageenan with 1% KCl gave gel having 400 g/cm² gel strength on which streaking is possible.

TABLE 2

Effect of κ-carrageenan and KCl concentration on gel quality and gel strength of the medium at pH 13.0

| Carrageenan and KCl concentration | Gel quality at pH 13.0 | Gel strength (g/cm²) |
| --- | --- | --- |
| 1% Carrageenan and 1% KCl | Soft gel | 350 |
| 1.5% Carrageenan and 1% KCl | Medium gel | 400 |
| 1.5% Carrageenan and 1.5% KCl | Hard gel | 515 |
| 2% Carrageenan and 1.5% KCl | Hard gel | 700 |
| 2% Carrageenan and 2% KCl | Hard gel | 715 |
| 2.5% Carrageenan and 1.5% KCl | Hard gel | 770 |

Example 10

Optimum concentration of κ-carrageenan and KCl required to obtain desired gel strength in the medium having pH 13.5, which is used to isolate extreme alkaliphilic bacteria, varying concentration of κ-carrageenan and KCl were used in the medium. Table 3 describes quality of gel obtained and gel strength of the medium. The culture medium containing 2% carrageenan with 1.5% KCl, 2.5% with 1.5% KCl and 3% with 1.5% KCl gave good and firm gels with gel strength of 435, 700 and 810 g/cm², respectively. However, lower κ-carrageenan concentration yielded soft gel on which streaking is not possible.

TABLE 3

Effect of κ-carrageenan and KCl concentration on gel quality and gel strength of the medium having pH 13.5

| Carrageenan and KCl concentration | Gel quality at pH 13.5 | Gel strength (g/cm²) |
| --- | --- | --- |
| 1.5% Carrageenan and 1% KCl | Soft gel | 230 |
| 1.5% Carrageenan and 1.5% KCl | Soft gel | 310 |
| 2% Carrageenan and 1.5% KCl | Hard gel | 430 |
| 2% Carrageenan and 2% KCl | Hard gel | 450 |
| 2.5% Carrageenan and 1.5% KCl | Hard gel | 700 |
| 3% Carrageenan and 1.5% KCl | Hard gel | 810 |

Example 11

Three types of carbon sources like glucose, sucrose and starch were used to identify the suitable carbon source for the isolation, purification and study of colony morphology of extreme alkaliphilic bacteria, which can be used for their identification. Sucrose containing media gave better growth of alkaliphiles with bigger colony size which resulted in easy purification of individual bacterium.

Example 12

Alkaliphilic bacteria were isolated from alkaline effluent collected from industries and also from alkaline soil. One gram of soil was suspended in 5 ml sterile distilled water and 100 μl of the resulting suspension or 100 μl of alkaline effluent was inoculated either by spreading or streaking on alkaline solid media having pH 12.0. The plates were incubated at 37° C. for 48 h. and the isolates were purified by repeated streaking.

Example 13

Isolated pure cultures obtained after repeated streaking were individually inoculated on the media plates having pH 10.0, 12.0, 13.0 and 13.5 and incubated for 24 and 48 h to observe their growth. This has established alkali tolerance of isolated cultures. Some of the isolates took longer time to grow at higher pH. Table 4 shows growth of different isolates on various pH with respect to incubation time. Culture No. 3, 6, 13 and 20 could grow at neutral as well as at alkaline pH and hence they are not obligate alkaliphiles. The rest are obligate alkaliphiles, amongst which, six bacterial cultures No. 2, 4, 11, 14, 16 and 18 could grow well at pH 13. Also, two bacterial cultures, No 4 and 16 could grow up to pH 13.5 after 5 days.

TABLE 4

Growth of various isolates of alkaliphiles on the solid media having different pH

| Culture No. | Incubation Period (h) | 7.5 | 8.0 | 9.0 | 10 | 11 | 11.5 | 12 | 12.5 | 13 | 13.5* |
|---|---|---|---|---|---|---|---|---|---|---|---|
| 1 | 24 |  | ++ | ++ | ++ | ++ | ++ | ++ | ++ |  |  |
|  | 48 |  | ++ | ++ | ++ | ++ | ++ | ++ | ++ |  |  |
| 2 | 24 |  | ++ | ++ | ++ | ++ | ++ | ++ | ++ | + |  |
|  | 48 |  | ++ | ++ | ++ | ++ | ++ | ++ | ++ | ++ |  |
| 3 | 24 | ++ | ++ | ++ | ++ | ++ | ++ | ++ | ++ |  |  |
|  | 48 | ++ | ++ | ++ | ++ | ++ | ++ | ++ | ++ |  |  |
| 4 | 24 |  | ++ | ++ | ++ | ++ | ++ | ++ | ++ | ++ | + |
|  | 48 |  | ++ | ++ | ++ | ++ | ++ | ++ | ++ | ++ | ++ |
| 5 | 24 |  | ++ | ++ | ++ | ++ | ++ | ++ | ++ |  |  |
|  | 48 |  | ++ | ++ | ++ | ++ | ++ | ++ | ++ |  |  |
| 6 | 24 | ++ | ++ | ++ | ++ | ++ | ++ | ++ | ++ |  |  |
|  | 48 | ++ | ++ | ++ | ++ | ++ | ++ | ++ | ++ |  |  |
| 7 | 24 |  | ++ | ++ | ++ | ++ | ++ | ++ | ++ |  |  |
|  | 48 |  | ++ | ++ | ++ | ++ | ++ | ++ | ++ |  |  |
| 8 | 24 |  | ++ | ++ | ++ | ++ | ++ | ++ | ++ |  |  |
|  | 48 |  | ++ | ++ | ++ | ++ | ++ | ++ | ++ |  |  |
| 9 | 24 |  | ++ | ++ | ++ | ++ | ++ | ++ | ++ |  |  |
|  | 48 |  | ++ | ++ | ++ | ++ | ++ | ++ | ++ |  |  |
| 10 | 24 |  | ++ | ++ | ++ | ++ | ++ | ++ | ++ |  |  |
|  | 48 |  | ++ | ++ | ++ | ++ | ++ | ++ | ++ |  |  |
| 11 | 24 |  | ++ | ++ | ++ | ++ | ++ | ++ | ++ | + |  |
|  | 48 |  | ++ | ++ | ++ | ++ | ++ | ++ | ++ | ++ |  |
| 12 | 24 |  | ++ | ++ | ++ | ++ | ++ | ++ | ++ |  |  |
|  | 48 |  | ++ | ++ | ++ | ++ | ++ | ++ | ++ |  |  |
| 13 | 24 | ++ | ++ | ++ | ++ | ++ | ++ | ++ | ++ |  |  |
|  | 48 | ++ | ++ | ++ | ++ | ++ | ++ | ++ | ++ |  |  |
| 14 | 24 |  | ++ | ++ | ++ | ++ | ++ | ++ | ++ | + |  |
|  | 48 |  | ++ | ++ | ++ | ++ | ++ | ++ | ++ | ++ |  |
| 15 | 24 |  | ++ | ++ | ++ | ++ | ++ | ++ | ++ |  |  |
|  | 48 |  | ++ | ++ | ++ | ++ | ++ | ++ | ++ |  |  |
| 16 | 24 |  | ++ | ++ | ++ | ++ | ++ | ++ | ++ | ++ | ++ |
|  | 48 |  | ++ | ++ | ++ | ++ | ++ | ++ | ++ | ++ | ++ |
| 17 | 24 |  | ++ | ++ | ++ | ++ | ++ | ++ | ++ |  |  |
|  | 48 |  | ++ | ++ | ++ | ++ | ++ | ++ | ++ |  |  |
| 18 | 24 |  | ++ | ++ | ++ | ++ | ++ | ++ | ++ | ++ |  |
|  | 48 |  | ++ | ++ | ++ | ++ | ++ | ++ | ++ | ++ |  |
| 19 | 24 |  | ++ | ++ | ++ | ++ | ++ | ++ | ++ |  |  |
|  | 48 |  | ++ | ++ | ++ | ++ | ++ | ++ | ++ |  |  |
| 20 | 24 | ++ | ++ | ++ | ++ | ++ | ++ | ++ | ++ |  |  |
|  | 48 | ++ | ++ | ++ | ++ | ++ | ++ | ++ | ++ |  |  |
| 21 | 24 |  | ++ | ++ | ++ | ++ | ++ | ++ | ++ |  |  |
|  | 48 |  | ++ | ++ | ++ | ++ | ++ | ++ | ++ |  |  |

*Growth at pH 13.5 after 5 days.
+ Growth; ++ good growth

Example 14

Isolated pure cultures of alkaliphiles obtained after repeated sub-culturing, were individually inoculated on the plates having varying salt concentration and incubated at 37° C. for 24 and 48 h to observe their growth. This has established their tolerance towards different salt concentration. Table 5 shows growth of different isolates in the presence of different salt concentration with respect to incubation time. The results indicated that all the alkaliphilic bacterial cultures could grow from 1% to 10% salt concentration. However, the culture No. 2, 3, 4, 5, 11, 16 and 19 could tolerate 10 to 15% NaCl and hence they can be classified as extreme haloalkaliphiles.

TABLE 5

Salt tolerance of various alkaliphilic bacteria

| Culture No | Incubation time (h) | Salt concentration (%) | | | | | | | |
|---|---|---|---|---|---|---|---|---|---|
| | | 1 | 2 | 3.5 | 5 | 7.5 | 10 | 12.5 | 15 |
| 1 | 24 | ++ | ++ | ++ | ++ |  |  |  |  |
|  | 48 | ++ | ++ | ++ | ++ | ++ | ++ |  |  |
| 2 | 24 | ++ | ++ | ++ | ++ | ++ | ++ | ++ |  |
|  | 48 | ++ | ++ | ++ | ++ | ++ | ++ | ++ | ++ |
| 3 | 24 | ++ | ++ | ++ | ++ | ++ | ++ | ++ |  |
|  | 48 | ++ | ++ | ++ | ++ | ++ | ++ | ++ |  |
| 4 | 24 | ++ | ++ | ++ | ++ | ++ | ++ | ++ |  |
|  | 48 | ++ | ++ | ++ | ++ | ++ | ++ | ++ |  |
| 5 | 24 | ++ | ++ | ++ | ++ | ++ | ++ | ++ |  |
|  | 48 | ++ | ++ | ++ | ++ | ++ | ++ | ++ |  |
| 6 | 24 | ++ | ++ | ++ | ++ | ++ | ++ |  |  |
|  | 48 | ++ | ++ | ++ | ++ | ++ | ++ |  |  |
| 7 | 24 | ++ | ++ | ++ | ++ | ++ | ++ |  |  |
|  | 48 | ++ | ++ | ++ | ++ | ++ | ++ |  |  |
| 8 | 24 | ++ | ++ | ++ | ++ | ++ |  |  |  |
|  | 48 | ++ | ++ | ++ | ++ | ++ |  |  |  |
| 9 | 24 | ++ | ++ | ++ | ++ | ++ | ++ |  |  |
|  | 48 | ++ | ++ | ++ | ++ | ++ | ++ |  |  |
| 10 | 24 | ++ | ++ | ++ | ++ | ++ |  |  |  |
|  | 48 | ++ | ++ | ++ | ++ | ++ |  |  |  |
| 11 | 24 | ++ | ++ | ++ | ++ | ++ | ++ | ++ | ++ |
|  | 48 | ++ | ++ | ++ | ++ | ++ | ++ | ++ | ++ |
| 12 | 24 | ++ | ++ | ++ | ++ | ++ |  |  |  |
|  | 48 | ++ | ++ | ++ | ++ | ++ |  |  |  |
| 13 | 24 | ++ | ++ | ++ | ++ | ++ |  |  |  |
|  | 48 | ++ | ++ | ++ | ++ | ++ |  |  |  |
| 14 | 24 | ++ | ++ | ++ | ++ | ++ |  |  |  |
|  | 48 | ++ | ++ | ++ | ++ | ++ |  |  |  |
| 15 | 24 | ++ | ++ | ++ | ++ | ++ |  |  |  |
|  | 48 | ++ | ++ | ++ | ++ | ++ |  |  |  |
| 16 | 24 | ++ | ++ | ++ | ++ | ++ | ++ | ++ | ++ |
|  | 48 | ++ | ++ | ++ | ++ | ++ | ++ | ++ | ++ |
| 17 | 24 | ++ | ++ | ++ | ++ | ++ |  |  |  |
|  | 48 | ++ | ++ | ++ | ++ | ++ |  |  |  |
| 18 | 24 | ++ | ++ | ++ | ++ | ++ | ++ |  |  |
|  | 48 | ++ | ++ | ++ | ++ | ++ | ++ |  |  |
| 19 | 24 | ++ | ++ | ++ | ++ | ++ | ++ | ++ | ++ |
|  | 48 | ++ | ++ | ++ | ++ | ++ | ++ | ++ | ++ |
| 20 | 24 | ++ | ++ | ++ | ++ | ++ | ++ |  |  |
|  | 48 | ++ | ++ | ++ | ++ | ++ | ++ |  |  |
| 21 | 24 | ++ | ++ | ++ | ++ | ++ |  |  |  |
|  | 48 | ++ | ++ | ++ | ++ | ++ |  |  |  |

++ = Good growth

Example 15

The alkaliphilic bacterial culture no. 16 formed smooth, round, convex and yellow colour pigmented small colony on alkaline solid media having pH 12.0. It could grow on alkaline solid medium having pH in the range of 8.0 to 13.5 in the presence of sodium chloride up to 15%. Microscopic examination illustrated it as Gram negative, motile and straight rods. It was catalase and oxidase positive, IMViC tests negative and produced acid from D-glucose, arabinose, D-maltose, D-fructose, sucrose and mannitol. Based on the colony characteristics, morphological and bio-chemical tests, the culture was identified as *Pseudomonas* spp. It was sensitive to chloramphenicol (30 µg), clindamycin (2 µg), erythromycin (15 µg), co-trimaxazole (25 µg) and gentamycin (10 µg) and resistant to ampicillin (10 µg), penicillin (10 units) and norfloxacin (10 µg).

Example 16

The alkaliphilic bacterial culture No. 21 formed smooth, round, and orange colour colonies on alkaline solid media having pH 12.0. It could grow on alkaline solid media having pH in the range of 8.0 to 12.5 and in the presence of sodium chloride containing media up to 10%. Microscopic examination confirmed it as Gram positive and straight rods. It produced acid from D-glucose, arabinose, adonitol, lactose, sorbitol, D-maltose, D-fructose, sucrose and R-mannitol. It also hydrolyzed starch and showed resistance to ampicillin (30 µg), gentamycin (50 µg) and sensitive to kanamycin (70 µg). The 16 s rRNA gene (partial sequence) of the isolate showed maximum homology with that of *Exiguobacteium* spp.

ADVANTAGES OF THE INVENTION

The advantages of the present invention are as following:
1) Providing a new solid culture medium for the isolation of alkaliphilic bacteria.
2) Identification of an alternate gelling agent to agar, which is cheaper, easily available and stable at extreme alkaline pH, greater than 12.5.
3) Isolation of alkaliphilic bacteria in the form of individual colonies.
4) Exploitation of promising individual alkaliphiles for industrial applications like enzymes, biopolymers and other value added products.
5) Exploitation of isolated cultures for bioremediation of alkaline effluents.
6) Exploitation of isolated halo-alkaliphilic cultures for bioremediation of alkaline effluents having high salt concentration.
7) Studies on biodiversity of cultivable alkaliphilic bacteria.

We claim:

1. A solid nutrient media composition having alkaline pH, useful for isolating and identifying alkaliphilic microorganisms in pure form, wherein the media composition per liter of distilled water consists essentially of 5-15 g of carbon source, 2.5 to 10 g of peptone, 2.5 to 10 g of yeast extract, 0.5 to 1.5 g of dipotassium hydrogen phosphate; 0.1 to 0.5 g of magnesium sulphate heptahydrate, 30 µl to 4 ml of super saturated solution of sodium hydroxide, 5 to 20 g of potassium chloride and 10 to 30 g of κ-carrageenan, wherein the said media has a pH of greater than 12.5 and a gel strength of greater than 200 g/cm$^2$.

2. A solid nutrient media composition according to claim 1, wherein the carbon source used is selected from the group comprising sucrose, glucose, starch.

3. A solid nutrient media composition according to claim 1, wherein the said media is stabilized at a pH ranging from 12.5 to about 13.5 by using κ-carrageen an as gelling agent.

4. A solid nutrient media composition according to claim 1, wherein the super saturated solution of sodium hydroxide alkali is used to maintain the pH of the medium in the range of 12.5 to 13.5.

5. A solid nutrient media composition according to claim 1, wherein a specific proportion of κ-carrageenan and potassium chloride is maintained in a weight ratio range of 1:2-2:3 to obtain the desired gel strength of 230-810 g/cm$^2$ of the said solid media at pH of 12.5-13.5.

6. A method of isolating and identifying alkaliphilic microorganisms in pure form using a solid nutrient media composition according to claim 1, wherein the said process comprising the following steps of:
   i. inoculating a suspension of alkaline soil sample and alkaline effluent by spreading technique on the solid nutrient media of claim 1 to obtain microbial plates with isolated colonies of alkaliphiles;
   ii. incubating the microbial plates as obtained from step (i) at 37±2° C. for a period of 24-72 hours;
   iii. purifying an individual colony from the plates as obtained from step (ii) and re-inoculating on a fresh solid medium and growing at 37±2° C. for a period of 24-72 hours;
   iv. transferring the individual pure alkaliphilic bacterial colony thus obtained from step (iii) on slants containing the same solid nutrient medium;
   v. identifying the bacterial culture colony as obtained from step (iv) using standardized cultural, morphological and biochemical tests and molecular methods;
   vi. studying alkaline tolerance, salt tolerance and other properties of cultivable alkaliphilic bacteria as obtained from step (v).

7. A method of isolating and identifying alkaliphilic microorganisms according to claim 6, wherein the individual colonies are purified based on their size of individual colonies being in the range of 0.5-3.0 mm, shape being selected from the group comprising flat, concave or convex and the pigments being selected from the group comprising translucent, white, cream or yellow.

8. A process for preparing a solid nutrient media composition having a gel strength of greater than about 230 g/cm$^2$ and having alkaline pH, wherein the said process comprising the following steps of:
   (a) preparing a culture medium by mixing the ingredients in the following proportions: 5 to 15 g of carbon source, 2.5 to 10 g of peptone, 2.5 to 10 g of yeast extract, 0.5 to 1.5 g of dipotassium hydrogen phosphate; 0.1 to 0.5 g of magnesium sulphate heptahydrate, 5 to 20 g of potassium chloride and 10 to 30 g of κ-carrageenan in one liter of distilled water;
   (b) sterilizing the media as obtained from step (a) at standardized conditions; and
   (c) adjusting pH of the medium as obtained from step (b) to greater than 12.5 using 30 µl to 4 ml of super saturated solution of sodium hydroxide.

* * * * *